United States Patent [19]

Lawson

[11] Patent Number: 5,374,365
[45] Date of Patent: * Dec. 20, 1994

[54] POLYPHENOL COMPOUNDS AND THEIR USE IN LUBRICANTS AND COATINGS

[75] Inventor: John R. Lawson, Manchester, England

[73] Assignee: Zeneca limited, London, England

[*] Notice: The portion of the term of this patent subsequent to Jun. 15, 2010 has been disclaimed.

[21] Appl. No.: 870,280

[22] Filed: Apr. 17, 1992

[30] Foreign Application Priority Data

Apr. 18, 1991 [GB] United Kingdom ............... 9108220
Apr. 18, 1991 [GB] United Kingdom ............... 9108223

[51] Int. Cl.$^5$ ............... C10M 133/30; C10M 133/08; C07C 251/40; C07C 211/27
[52] U.S. Cl. ............... 252/51.5 R; 106/14.15; 106/14.31; 106/14.37; 564/265; 564/325; 564/337; 564/390
[58] Field of Search ............... 564/265, 325, 337, 390; 252/51.5 R; 106/14.15, 14.31, 14.37

[56] References Cited

U.S. PATENT DOCUMENTS

| | | | |
|---|---|---|---|
| 2,750,416 | 6/1956 | Exner et al. | 260/570.9 |
| 2,802,820 | 8/1957 | Zech | 260/211 |
| 4,457,790 | 7/1984 | Lindent et al. | 148/6.15 R |
| 4,612,130 | 9/1986 | Landry et al. | 252/51.5 R |
| 5,219,481 | 6/1993 | Lawson | 252/51.5 R |

FOREIGN PATENT DOCUMENTS

| | | |
|---|---|---|
| 0276072 | 7/1984 | European Pat. Off. |
| 0206716 | 12/1986 | European Pat. Off. |
| 0276072 | 7/1988 | European Pat. Off. |
| 0276073 | 7/1988 | European Pat. Off. |
| 877062 | 9/1961 | United Kingdom |

OTHER PUBLICATIONS

Kaemmerer et al. "Preparation of Phenolic Compounds, etc" *Makromol. Chem.*, 180(7) 1635-50 Abst. in *Chem. Abst* 91(21):169491a.

*Primary Examiner*—Peter O'Sullivan
*Attorney, Agent, or Firm*—Cushman, Darby & Cushman

[57] ABSTRACT

A polyphenol compound wherein the aromatic rings are linked by direct bonds or by a divalent link in the ortho position relative to the —OH group and the end aromatic rings contain either oximino substituents or substituted alkylaminomethyl substituents in the ortho position. The compound can be coated onto a metal surface to give improved corrosion resistance. The metal surface can be zinc-coated steel or zinc phosphated steel. The polyphenol compound can be the only coating material or can be incorporated into a surface coating composition such as a paint.

11 Claims, No Drawings

POLYPHENOL COMPOUNDS AND THEIR USE IN LUBRICANTS AND COATINGS

The present invention relates to a new class of compound, compositions containing such compounds and the use of the compounds or compositions, particularly to improve the resistance of a metal to oxidative, and/or other, deterioration.

Metal surfaces which are exposed to weather are particularly vulnerable to oxidative deterioration and require protection. Oxidative deterioration of a metal may be reduced by coating the metal with an anti-corrosive coating composition, for example by coating iron and steel to reduce rusting.

Coating compositions which can be used to reduce corrosion frequently, but not always, are based on film forming organic polymeric materials. The coating compositions generally also contain a mixture of pigments and extender solids, at least one of which is effective in retarding corrosion of the substrate metal. Pigments containing lead, in particular red lead, and hexavalent chromium, for instance zinc potassium chromate, are efficient anti-corrosive pigments and have been widely used with success. However, there is a growing awareness of the toxicity of lead and hexavalent chromium and this has already resulted in some replacement of these materials by alternative materials. This trend is expected to accelerate when alternative materials are developed which have a performance matching that of lead and hexavalent chromium. Zinc phosphate is considered non-toxic, and is extensively used as an anti-corrosive pigment. However, deficiencies in the performance of zinc phosphate are widely reported, in particular its inability to prevent rust creep from damage to the coating. Although slightly soluble metal salts of organic acids are extensively used as corrosion inhibiting additives in aqueous reservoir systems, surprisingly these materials are not widely used as corrosion inhibiting pigments in surface coating compositions. Pigments recently proposed as corrosion inhibitors in metal coating compositions, particularly for ferrous metals, include magnesium azelate (GB 15555468), zinc and lead 5-nitroisophthalates (GB 1531093), zinc cyanurate (U.S. Pat. No. 4,329,381) and zinc and lead N-phenylglycinate (DE 3306064). Barium salts of hydroxy carboxylic acids such as salicylic acid, have also been proposed (U.S. Pat. No. 4,304,707). However, barium salicylate is soluble in water at a level of greater than 10% w/w, and hence is liable to be leached from a coating containing barium salicylate. The salts of a divalent metal and a hydroxycarboxylic acid containing a fused ring system have also been disclosed as having corrosion inhibiting properties (EP 289155). Many of the foregoing metal salts are indicated to be very effective, and also to be useful in improving the performance of zinc phosphate when present at low levels.

In addition to the various metal salts which can be used as corrosion inhibitors, there have also been proposals to use organic compounds as corrosion inhibitors. Organic compounds proposed for use as corrosion inhibitors include oximes such as benzaldoxime (GB 1365291), salicylaldoxime, 2-hydroxy-5-alkylbenzaldoximes in which the alkyl group contains 7 to 13 carbon atoms (EP 125025), bis-oximes (EP 178850) and hydroxy oxime metal complexes (EP 206716), di- and tri-hydroxybenzene derivatives (GB 676632, GB 1045118, U.S. Pat. No. 2,429,905 and EP 239288), alkenyl or alkyl succinic acid or anhydride and derivatives thereof (GB 1055337 and U.S. Pat. No. 4,326,987) and polyesters and functionally terminated derivatives thereof (U.S. Pat. Nos. 3,415,766, 3,574,566 and EP 277711).

Although a wide range of materials have been proposed to provide corrosion inhibition, it is still desirable to find systems which provide improved corrosion inhibition characteristics.

It has been proposed to use 2-hydroxy benzylamine for protecting metal surfaces. Thus, EP 276072 discloses and claims a composition which has a pH between 2 and 6, and contains at least 0.01% by weight of a water-soluble or water-dispersible metal chelating compound of general formula:

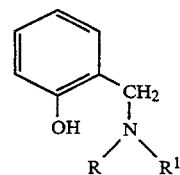

wherein R is an alkanol moiety selected from ethanol and propanol moieties and $R^1$ is H, alkyl, aryl or hydroxyalkyl. The phenol ring and alkanol moieties may be substituted with a non-interfering functionally, which is stated to be that which would not substantially interfere with the intended use of the compounds as described in EP 276072, namely to deposit a corrosion inhibiting and adhesion promoting coating on a metal substrate.

We have now found a class of organic compound which is useful in providing surface protection properties.

According to the present invention there is provided a compound of the general formula (I):

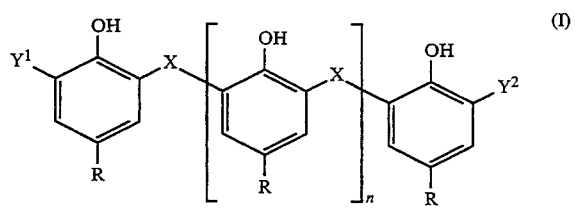

wherein
R is a hydrogen atom or a substituted or unsubstituted group selected from hydrocarbon, hydrocarbonoxy, hydrocarboncarbonyl, hydrocarbonoxycarbonyl, and hydrocarboncarbonyloxy groups;
$Y^1$ is a group

or a group

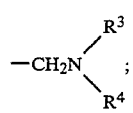

$Y^2$ is a group when Y¹ is a group

or a group

when Y¹ is a group

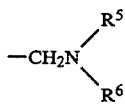

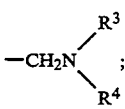

R¹ and R² are each independently hydrogen or a substituted or unsubstituted hydrocarbon group;
R³ and R⁵ which may be the same or different are amino $C_{1-4}$ alkyl, mercapto $C_{1-4}$ alkyl or hydroxy $C_{1-4}$ alkyl;
R⁴ and R⁶ which may be the same or different are hydrogen, hydrocarbon having up to 20 carbon atoms or as defined for R³ and R⁵;
X is a direct bond or is a divalent linking group; and
n has a value of zero or has a positive value.

Thus, in one embodiment of the invention there is provided a compound of formula II

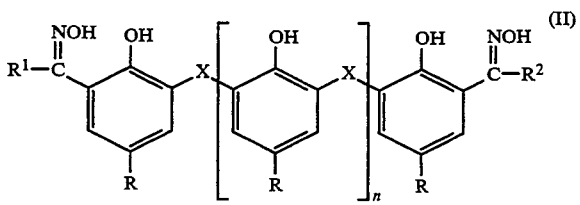

wherein R, R¹, R² and n are all as hereinbefore defined.

If any of the groups R, R¹ and R² is substituted, there may be more than one substituent and these may be the same or different. The substituent groups may be hydroxy, halogen, hydrocarbonoxy, hydrocarbonoxycarbonyl, hydrocarboncarbonyloxy, nitro or nitrile groups.

Typically the groups R, R¹ and R² are unsubstituted. The groups R¹ and R² are conveniently the same. The groups R¹ and R² can be alkyl or aryl groups or a combination of both as in alkaryl and aralkyl. The groups R¹ and R² may contain up to 20 carbon atoms, for example not more than 10 carbon atoms. Preferably both R¹ and R² are $C_{1-4}$ lower alkyl such as methyl, and especially hydrogen.

The group R is preferably other than a hydrogen atom. The group R preferably is, or includes, a hydrocarbon group having at least six carbon atoms. The group R may be, or include, a hydrocarbon group containing 30 carbon atoms or more but generally little benefit is gained if the group R is, or contains, a hydrocarbon group of more than 24 carbon atoms and hence typically the group R is, or contains, a hydrocarbon group of not more than 24 carbon atoms. In general, the group R contains not more than 18 carbon atoms. We have obtained useful results with compounds of formula (I) in which the group R is an alkyl group and especially an alkyl group containing at least 8 carbon atoms.

If the groups R R¹ and R² are, or contain, an alkyl group, they may be a mixture of alkyl groups, for example a mixture of isomers or alkyl groups containing different numbers of carbon atoms, or may be a mixture of isomers of alkyl groups which also contain different numbers of carbon atoms. The groups R, R¹ and R² if they are, or contain, alkyl groups, especially alkyl groups containing at least six carbon atoms, typically contain branched chain alkyl groups.

If the group X is a divalent linking group it may be a substituted or unsubstituted hydrocarbon group or may be, or may include, at least one heteroatom, for example as in a sulphoxide, sulphone, carbonyl or imine linking group. The substituents which may be present in the group X may be any of the substituents disclosed previously herein as possible substituents in the groups R, R¹ or R². Preferably the group X is a direct bond or a divalent unsubstituted hydrocarbon linking group, especially a $C_{1-6}$ alkylene group such as methylene. It is especially preferred that X is a direct bond.

If the value of n is zero, the compound of the general formula (I) is a bis-phenol derivative and is specifically a compound of the general formula (III)

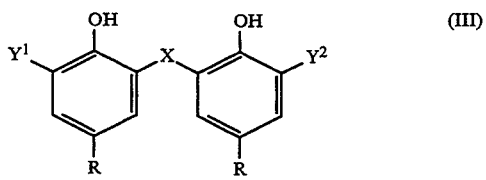

where R, Y¹, Y² and X are all as hereinbefore defined.

When X is a direct bond the compound of the general formula (I) is conveniently prepared by a process which includes oxidation of a 4-substituted phenol and typically such a process produces a mixture of compounds, for example a mixture of a dimer and higher oligomers. With such a mixture, the value of n is an average value and this average value is generally not an integer. Hence, generally n has a value of greater than zero and is not an integer. Typically the compound of formula (I) is a mixture of compounds where the value of n does not exceed 10 in any oligomer. The average value of n generally is not greater than five. Usually, the average value of n is at least one and does not exceed four, and particularly the average value of n is between one and three.

A typical compound of general formula (II) in accordance with the present invention is one in which R is a mixture of branched alkyl groups containing at least eight carbon atoms and not more than 18 carbon atoms, R¹ and R² are both hydrogen atoms, X is a direct bond, a methylene group or an imine group and n has an average value of between one and three.

A particular compound of general formula (II) is one in which R is a mixture of branched nonyl groups, R¹ and R² are both hydrogen atoms, X is a direct bond and n has an average value of between one and three.

In a further embodiment of the invention there is provided a compound of the general formula IV

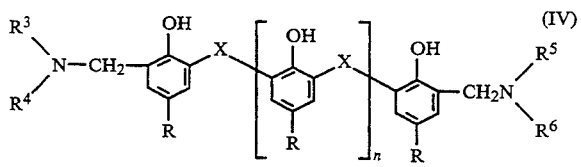

wherein R, $R^3$ to $R^6$ and n are all as hereinbefore defined.

Preferably, $R^3$ and $R^5$ are each $C_{1-4}$ alkyl and especially methyl. It is also preferred that $R^4$ and $R^6$ are amino $C_{1-4}$ lower alkyl, mercapto $C_{1-4}$ lower alkyl and especially hdyroxy $C_{1-4}$ lower alkyl. Examples of such groups are 2-mercaptoethyl, 2-aminoethyl, 2-hydroxyethyl and 2-hydroxypropyl.

The groups $R^3$ to $R^6$ may also be the same, especially 2-hydroxyethyl or 2-hydroxypropyl.

A particular compound of general formula IV is one in which R is a mixture of branched nonyl groups, $R^3$ and $R^5$ are methyl, $R^4$ and $R^6$ are 2-hydroxyethyl and X is a direct bond.

The compounds of the general formula (II) can be prepared from the corresponding aldehyde or ketone.

Thus, as a further aspect of the present invention there is provided a compound of the general formula (V):

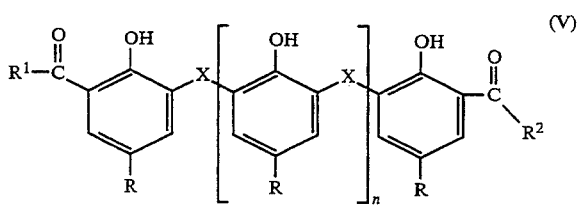

where R, $R^1$, $R^2$, X and n are all as hereinbefore defined.

Preferably the groups $R^1$ and $R^2$ are both hydrogen atoms and the compound of formula (V) is a di-aldehyde.

A compound of the general formula (V) can be reacted with hydroxylamine or a hydroxylamine salt to obtain an oxime, preferably a dioxime.

Thus, as a further aspect of the present invention, a compound of the general formula (V) is reacted with a sufficient quantity of a hydroxylamine or hydroxylamine salt to obtain a dioxime of the general formula (II).

The reaction is preferably effected using hydroxylamine or hydroxylamine salt in an amount greater than the stoichiometric amount required to form a dioxime. The reaction is conveniently effected by adding a solution of hydroxylamine or hydroxylamine salt to the compound of the formula (V) conveniently suspended or dissolved, in a suitable liquid medium. The compound of formula (V) may be suspended in a liquid such as industrial methylated spirits, dichloromethane, chloroform, carbon tetrachloride toluene, and alkanols particularly lower alkanols such as methanol, ethanol, propanol and butanol.

The reaction is desirably effected at an elevated temperature which is typically at least 50° C. and may be as high as 120° C. and preferably is not more than 100° C., and conveniently is the reflux temperature of the mixture. The reaction is effected for a time which is typically at least 30 minutes and may be 10 hours or more but conveniently is at least one hour and not more than six hours.

The dioxime product may be recovered by evaporating the reaction solvent, for example at ambient temperature under reduced pressure. The crude reaction product may be purified using known techniques. A convenient method of purification is to dissolve the crude product in a suitable solvent, for example ethyl acetate, dichloromethane, chloroform, carbon tetrachloride, toluene and alkanols, wash the solution with water to remove water soluble impurities, separate, dry the solution of the product and finally remove the solvent by distillation. Alternatively, if the reaction solvent used is water miscible, useful purification can be achieved by pouring the product mixture directly into an excess of cold water, filtering off the precipitate and drying.

The compounds of the general formula IV can be prepared from the corresponding 4-substituted phenol dimer, oligomer or mixture. Typically, such compounds can be prepared using a Mannich reaction in which the dimer, oligomer or mixture is reacted with a substituted amine in the presence of formaldehyde. The dimer, oligomer or mixture is a compound, or mixture, of the general formula VI as described hereinbefore.

The compound of the general formula VI is typically reacted with the amine and formaldehyde in the proportions of one mole of the compound of the general formula (VI), at least two moles of amine and not more than a molar equivalent of formaldehyde relative to the amine. The amine is a compound of the formula $R^3R^4NH$, or of the formula $R^5R^6NH$, or a mixture thereof wherein $R^3$, $R^4$, $R^5$ and $R^6$ are all as previously defined herein.

Preferred compounds in accordance with the present invention are those in which $R^3$ and $R^5$ are the same and $R^4$ and $R^6$ are the same. Such compounds can be prepared by the reaction of the compound of the general formula VI with two moles of the amine $R^3R^4NH$ in the presence of not more than a molar equivalent, relative to the amine, of formaldehyde. If it is desired to prepare a compound in which $R^3$ and $R^5$ are different and/or $R^4$ and $R^6$ are different, such compounds can be obtained by reacting the compound of the general formula VI either with a mixture of $R^3R^4NH$ and $R^5R^6NH$ or by reacting with $R^3R^4NH$ and $R^5R^6NH$ in sequence, in the presence of formaldehyde.

The reaction can be effected under any suitable conditions and is conveniently effected at a slightly elevated temperature, for example up to 100° C. and typically not more than 60° C. The reaction is preferably effected in a liquid medium using a suitable solvent. Solvents which may be used include alcohols, ethers, ketones and esters. The formaldehyde is typically added as an aqueous solution. Hence, it is preferred that the reaction is effected with water, a suitable solvent being industrial methylated spirits.

The reaction time is dependent on the temperature used and is typically from 0.5 up to 20 hours, for example at least one hour and not more than 15 hours.

The reaction product is generally soluble in the reaction solvent from which it may be recovered by evaporation of the solvent. The product may be purified by being dissolved in a suitable solvent, preferably a solvent which is essentially immiscible with water, washed with water to remove water-soluble impurities, the solution dried and the solvent removed, for example by evaporation.

Amines which may be used are preferably hydroxyalkylamines including ethanolamine, di(ethanol)amine, methylethanolamine, 2-hydroxypropylamine and other hydroxy lower alkylamines.

Compounds of formula (V) in which the groups $R^1$ and $R^2$ are both hydrogen can be prepared from the corresponding bis-phenol or poly-phenol of formula (VI).

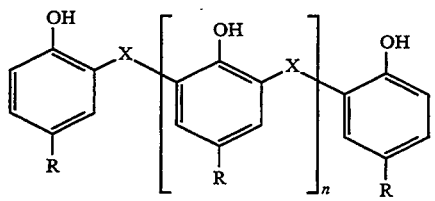

by reaction with hexamethylenetetramine and hydroysis of the intermediate product, where R, X and n are all as defined.

The reaction with hexamethylenetetramine is preferably carried out under conditions to form a Schiff's base which is then hydrolysed by reaction with an aqueous acid. The proportion of hexamethylenetetramine used should be sufficient to form the desired di-aldehyde on hydrolysis. The reaction is effected at an elevated temperature which is typically at least 50° C., particularly at least 80° C. and especially at least 100° C. The reaction temperature should not be so high as to cause breakdown of the bis-phenol or poly-phenol of formula (VI) and hence preferably does not exceed 180° C. and especially is not more than 150° C. and conveniently is the reflux temperature of the mixture. The reaction is continued to give essentially complete reaction and especially is effected for a time of at least one hour, particularly at least two hours and especially at least four hours. A reaction time of not more than 20 hours is generally not required and particularly the reaction time is not more than 15 hours and especially not more than 12 hours. As will be appreciated, the reaction time and temperature are related, a shorter required time being required at higher reaction temperatures. The reaction is preferably effected in solution in a suitable solvent such as glacial acetic acid, cellosolve and high boiling alcohols.

The Schiff's base which is formed initially may be hydrolysed using an aqueous acid, for example sulphuric acid. The aqueous acid may be relatively concentrated, for example between 6 N and 12 N. The hydrolysis is effected at an elevated temperature which is typically at least 50° C. The temperature of hydrolysis generally does not exceed 100° C. The time of the hydrolysis should be sufficient to give a substantial extent of reaction to form the desired di-aldehyde. Preferably the reaction time is at least 30 minutes and especially at least one hour. In general a reaction time of more than 10 hours is not required. The di-aldehyde reaction product can be obtained by cooling the reaction mixture, adding a suitable solvent which is immiscible with water, washing and drying the solution of the reaction product and then evaporating the solvent from the solution of the reaction product.

The reaction product may be converted into the dioxime of the general formula (II) without being subjected to any additional purification beyond that achieved by solvent extraction, washing and drying.

Other procedures for the preparation of aldehydes may be used but generally are less preferred. An alternative procedure is to react a phenol of the general formula (VI) with formaldehyde and an arylamine followed by oxidation and hydrolysis, such a process being described in more detail in British patent specification 1563206.

If the di-oxime of the general formula (II) is a ketoxime this may be obtained from a ketone derivative of the general formula (V). A ketone derivative may be obtained from a phenol of the general formula (VI) by acylation of the phenol group, followed by rearrangement to give a ketone group in each end ring, followed by hydrolysis as a final stage, if necessary.

A compound of the general formula (V) in accordance with the further aspect of the present invention is one in which R is a mixture of branched nonyl groups, $R^1$ and $R^2$ are both hydrogen atoms, X is a direct bond and n has an average value of between one and three.

Bis-phenols or poly-phenols of the general formula (VI) may be obtained from the corresponding 4-substituted phenol, particularly 4-alkylphenol by an oxidation process. The oxidation is conveniently effected by stirring a solution of the 4-substituted phenol in a water-immiscible solvent with an aqueous solution containing of a mixture of metal salts giving a redox mixture and passing a stream of air through the mixture. Any suitable mixture of metal salts can be used and we have obtained a satisfactory result using a mixture of copper (I) chloride, copper (II) chloride and iron (II) chloride. The solution may have a high halogen, particularly chlorine, ion concentration, for example at least 1 M in halogen ion, particularly at least 2 M in halogen ion, for example at least 5 M in halogen ion. The desired halogen ion concentration may be achieved by the addition of an alkali metal halide or an ammonium halide, for example sodium chloride. The aqueous solution of metal salts is prepared in a non-oxidising atmosphere, conveniently nitrogen, and an elevated temperature may be used, for example 40° to 60° C., to increase the rate of reaction. The extent of the oxidation can be monitored by gas chromatography to detect residual quatities of the 4-substituted phenol. It is preferred to continue the oxidation until the level of residual 4-substituted phenol is less than 10% of the original quantity of the 4-substituted phenol.

The oxidation is conveniently effected at an elevated temperature, for example 40° to 60° C. After passing air through the mixture for at least 30 minutes, preferably at least one hour, for example two hours, the passage of air may be terminated. The mixture is maintained, with stirring, at the elevated temperature for a prolonged period which is at least one day and may be several days, for example up to 25 days and conveniently 10 to 20 days. The reaction mixture is then allowed to cool and the organic and aqueous phases allowed to separate. The organic phase is then washed, preferably with an aqueous acid and thereafter the organic phase is dried and finally the solvent is removed by evaporation to give the oxidation product, which may be a liquid or a solid depending on the value of n and the nature of the group R.

The product obtained is an oligomeric 4-substituted phenol and typically is a mixture of oligomers in which the value of n is zero or has a value of up to ten. In general the product consists predominantly of materials in which the value of n is zero, one, two or three, together with a minor amount of materials in which the value of n is greater than three and generally is four or five. The product is typically one in which the average value of n is not more than four and especially is at least one and not more than three.

The mixture of oligomeric 4-substituted phenols obtained may be used to prepare, in turn, a di-aldehyde (or di-ketone) and a dioxime as described previously herein, or the mixture of oligomeric 4-substituted phenols may be used to prepare, for example, the bis(alkyl-2-hydroxyethylamine methyl) derivatives of general formula IV.

We have found that the compounds of the present invention are useful in providing surface protection properties.

Thus, in accordance with a further aspect of the present invention there is provided a process which comprises contacting at least part of a surface of a metal with a compound of any of general formulae (I), (II), (III) (IV), (V) and (VI) as hereinbefore defined.

The compound is particularly a dioxime of the general formula (II where X is a direct bond or divalent linking group or the compound is a bis(alkyl-2-hydroxyethylamino methyl) derivative of the general formula (IV where X is a direct bond.

The process of this further aspect of the present invention is especially suitable for the corrosion inhibition of iron, zinc, copper, tin and aluminium and in particular mild steel and the zinc surface of a galvanised steel.

The metal is contacted with the compound by treating the metal directly with the compound, particularly dialdoxime, although it is generally preferred to apply the compound to the metal surface in the form of a solution in a suitable solvent. The dioxime is useful when used to provide a protective coating in its own right. However, the compound may be used as a metal pre-treatment before the application of a surface coating, or may be incorporated into a surface coating composition.

Conventional organic solvents may be used for the compounds and these include, for example, alcohols, ethers, ketones and aliphatic and aromatic hydrocarbons. Especially preferred solvents are those having good wetting and drying properties and include for example ethanol, propano-2-ol, toluene, xylene, chloroform and 1,1,1-trichloroethane. A mixture of organic solvent with water may be used, for example when the organic solvent is a lower alcohol such as ethanol, propanol or propan-2-ol. Compounds of the general formulae (I), (II), (III), (IV), (V) and (VI) are essentially insoluble in water and hence if water is used as the liquid medium the compounds are used as a dispersion in the water.

The compounds of the present invention are typically solids and are preferably contacted with at least part of a surface of a metal as a solution or dispersion in a suitable liquid medium.

Thus, as a yet further aspect of the present invention there is provided a composition which comprises
a) a liquid solvent or dispersant or a surface coating composition and
b) a compound as hereinbefore defined.

Component a) of the coating composition may be a liquid in which component b) is dissolved or dispersed. Suitable liquids include aliphatic, cycloaliphatic and aromatic hydrocarbons, halogenated hydrocarbons, alcohols, esters and ketones, many of the compounds which are component b) being soluble in such liquids. Alternatively, the liquid can be water in which the compounds which are component b) are generally insoluble and hence, when component a) is water, the composition is generally a dispersion of component b) in water. Alternatively, the liquid may be a mixture such as an aqueous alcohol. If a liquid dispersant is used, this may include a suitable surfactant to aid dispersion of component b) in the liquid. Component a) may be a lubricating material, for example liquid paraffin or a synthetic polyalkylene glycol lubricant.

Alternatively, component a) is a surface coating composition, for example a film forming binder system. The film forming binder system which can be used as component (a) of the coating composition may be a paint (primer), a lacquer; a resin or other protective coating. Thus, component (a) may be a solvent-based surface coating composition, for example a cellulose/solvent based primer paint such as those used for car "touch-up" paints. The compound which is component (b) of the coating composition is generally soluble to at least some extent in the solvents used for such primers and typically is added as a solid when being incorporated into such a primer paint system. Alternatively, component (a) may be an aqueous emulsion surface coating system, for example a primer or protective coating based on polymer latices such as for example acrylic and styrene/acrylic latices and vinyl acrylic copolymer latices including acrylate modified vinyl chloride-vinylidene chloride copolymer latices, and the compound which is component (b) may be used as a dispersion or suspension in such aqueous systems. The surface coating composition may be an alkali-removable protective coating composition of the addition polymer type in which the polymer contains carboxyl groups.

The film forming binder system which may be used as component (a) of the composition preferably contains an organic polymer and in general any such polymer used in the paint industry may be included in the composition. Thus, the suitable film forming binders include, for example, an alkyd resin, an epoxy resin, an oleoresin, a latex rubber, a chlorinated rubber, a vinyl resin such as polyvinylacetate or polyvinyl butyral, a polyurethane, a polyester, an organic or inorganic silicate, a polyamide or an acrylic polymer. It will be appreciated that the composition can include two or more compatible film forming polymers. The composition may also include an extender or plasticising resin, such as a hydrocarbon resin, or a coal tar derivative.

The film forming binder system which may be used as component (a) of the coating composition of the present invention can include homopolymers and copolymers of the following:

vinyl chloride vinylidene chloride, vinyl esters of alkanoic acids having from 1 to 18 carbon atoms in the alkyl group, especially vinyl acetate, alkyl acrylates and methacrylates having from 1 to 18 carbon atoms in the alkyl group, acrylamide and substituted acrylamides, acrylonitrile, and methacrylonitrile, monoethylenically unsaturated hydrocarbons, for example ethylene, isobutene, styrene and alpha-methyl styrene.

Example of polymers usable when component (a) is a film forming binder system are "acrylic polymers", by which is meant those polymers comprising predominantly units of alkyl acrylates and/or methacrylates having from 1 to 12 carbon atoms in the alkyl group, sometimes containing an acid functionally by virtue of containing polymerised units of one or more aliphatic unsaturated alpha-beta unsaturated carboxylic acids. Polymers of this type are described in European Patent Application No 0115694.

Other examples of polymers usable when component (a) is a film forming binder system are copolymers of (i) vinyl chloride, (ii) vinylidene chloride and (iii) one or more alkyl acrylates or alkyl methacrylates having from 1 to 12 carbon atoms in the alkyl group; such polymers may optionally also contain polymerised units of one or more aliphatic alpha-beta unsaturated carboxylic acids, Copolymers of this type are described generally and specifically in the specification of UK Patent No 1558411.

Alkyd containing resins are extensively used as the film forming binder in paint systems and the composition may be one in which component (a) is a film forming binder system which is, or contains, an alkyd containing resin, particularly an oil-modified alkyd.

The polymer or polymers which is, or are, used when component (a) is a film forming binder system, is usually used in an amount of from 5 to 60% (based on weight in grams of the polymers per 100cm$^3$ of the composition), and more usually 10 to 40%. The polymer may be dissolved or colloidally dispersed (that is exist as an emulsion, with an average particle size usually below two micrometres) in a suitable liquid carrier medium.

Component (a) may be any material which can be contacted with a surface either to provide a coating thereon or to provide lubrication. Thus, component (a) may be a natural oil or grease which has been derived from animals or plants, such as, for example, lanolin or rape seed oil. Alternatively, component (a) may be a petroleum refined product such as a lubricating oil, turbine oil, fuel oil, gasoil or grease, which are used in circumstances in which they contact, if only temporarily, a metal surface.

Component (b) of the composition of the present invention can be a compound of general formula (I), (II), (III), (IV), (V) or (VI) and is preferably a dioxime of general formula (II) as hereinbefore defined, or an amine formaldehyde reaction product of general formula (IV) as hereinbefore defined.

The compositions of the present invention can be contacted with at least part of a surface of a metal and we have found that the coated surface has an increased resistance to corrosion. The compositions are suitable for the corrosion inhibition of iron, zinc, copper, tin and aluminium, particularly mild steel and the zinc surface of galvanised steel.

The use of the composition of the present invention to provide a corrosion inhibiting coating may be combined with a conventional corrosion inhibition treatment such as, for example, the phosphating of iron. Furthermore, the composition may include, in addition to the compound which is component (b), other materials, particularly those which have been proposed as corrosion inhibitors. Thus, the composition may include a metal oxide or as an alternative to, or in addition to, the metal oxide, the composition may also include a metal phosphate, particularly a phosphate of the metal which is present in the metal oxide.

Thus, as a further aspect of the present invention the composition may also include at least one of a metal oxide and a metal phosphate.

The composition of the present invention may be a lubricant composition in which component (a) is a lubricating oil or a grease. We have found that such compositions give resistance to corrosion and/or improved anti-wear characteristics when used in contact with moving metal surfaces.

The composition of the present invention typically contains from 0.1 to 30% by weight of the compound relative to the total volume of the composition and preferably the compound is present in an amount of 0.1 to 5% w/w. If component (a) of the composition is an emulsion of a film forming binder system in a liquid medium, the compound which is component (b) may give a useful effect when dispersed in the emulsion in an amount of from 0.1 to 15% w/w. If the composition is a lubricant composition the compound is typically present in such a composition in an amount of from 0.1 up to 10% wt/wt, preferably from 0.5 to 6% wt/wt.

In addition to the compound of the present invention and the liquid solvent or dispersant or the surface coating composition, the composition of the present invention may include various other ingredients such as those commonly employed in the film forming coating compositions such as defoamers, rheology control agents, thickeners, dispersing and stabilising agents (usually surfactants), wetting agents, extenders, fungicides, pigments or colorants of one sort or another, coalescing solvents, plasticisers, and anti-freeze agents. Furthermore, as noted previously herein, the composition may also include one or more known corrosion inhibitors.

The composition of the present invention may be prepared using any one of the techniques which have been used for incorporating solids into a liquid or plastic medium in which the solid is essentially insoluble. Thus, if component (a) is a film forming coating composition, techniques for preparing paint compositions may be used, for example by mixing components either in a grinding apparatus or pre-mixing the components and then grinding. The compound of the present invention and any optional metal oxide, metal phosphate or other corrosion inhibitor, may be incorporated into the surface coating composition at any convenient stage, for example during the grinding together of the components of the paint formulation.

As noted previously herein, the composition of the present invention may be coated onto a metal to provide a corrosion inhibiting coating on the metal.

Thus, as a further aspect of the present invention there is provided a process which comprises contacting, for example by coating, at least part of a surface of a metal with a composition as hereinbefore defined.

The process of the present invention results in a coated surface which typically has an increased resistance to corrosion and is especially suitable for the corrosion inhibition or iron, zinc, copper, tin and aluminium, particularly mild steel and the zinc surface of a galvanised steel.

The composition may be applied to the metal surface in conventional manner, for example by dipping, spraying or brushing. The temperature of the application may be any suitable temperature for example from 0° to 50° C.

The metal surface which is coated with the composition may be brightly polished and/or freshly cleaned, but a lightly rusted surface may be coated by the process of the present invention. Thus the composition may be coated onto a surface in an "as received" condition, and it may be unnecessary for the surface to be freshly cleaned or brightly polished.

The process of the present invention provides a corrosion inhibiting coating on the surface of a metal and may be combined with conventional corrosion inhibition treatments such as the phosphating of iron.

The process of the present invention may be used to provide corrosion inhibition as a pre-treatment before application of a known surface coating. Thus the coating step may be used, for example, to provide temporary protection whilst the metal is being transferred from one site to another. Hence the process of the present invention may be used for the temporary protection of a metal surface and the protective coating subsequently removed before or during further processing.

A metal surface coated in accordance with the process which is a further feature of the present invention has an improved resistance to corrosion.

Thus, as a yet further feature of the present invention there is provided a metal article, at least part of one surface of which has a coating which is a compound of general formula (I), (II), (III), (IV), (V) or (VI). Preferably the coating is a dioxime of general formula (I) as hereinbefore defined or which is a composition as hereinbefore described, preferably one which contains a dioxime as hereinbefore defined. Alternatively, the coating is preferably an amino formaldehyde reaction product of general formula (IV) as hereinbefore defined or which is a composition containing a compound of general formula IV as hereinbefore defined.

The surface of the metal is preferably coated with a composition which contains a compound of general formula I and a known corrosion inhibitor.

As a yet further aspect of the present invention the composition is a lubricant composition in contact with metal surfaces which are in relative motion. The lubricant composition provides improved resistance to corrosion and/or anti-wear characteristics in such a system.

Various aspects of the present invention are set out in more detail hereafter in the following illustrative examples in which all parts and percentages are by weight unless otherwise stated.

EXAMPLE 1 a. Preparation of poly(4-nonylphenol)

A mixture containing copper (I) chloride (7.8 parts by weight), sodium chloride (50 parts by weight), and water (100 parts by weight) was stirred and heated to between 48° and 52° C. under an atmosphere of nitrogen. Copper (II) chloride (3.6 parts by weight) and iron (II) chloride (3.6 parts by weight) were then added, followed by more water (100 parts). After stirring this mixture for five minutes, a clear solution was obtained.

A solution containing 4-nonylphenol (100 parts by weight) dissolved in n-hexane (480 parts by weight) was added, all at once, to the stirred solution of metal halides at 50°±2° C. prepared as described previously.

Stirring of the resulting mixture was continued at 50°±2° C. for two hours whilst forcing a current of air through the reaction mixture. After this time the current of air was stopped, and the reaction mixture was stirred for ten days at 50°±2° C. After this time the reaction mixture was cooled, stirring was stopped and the aqueous and organic layers were allowed to settle and were then separated. The organic layer was washed with aqueous 0.5 N acetic acid (200 parts) and then dried over anhydrous magnesium sulphate. The n-hexane was evaporated under reduced pressure (20-25 Torr) to yield 89 parts by weight of a dark brown viscous liquid. Analysis of this product by proton N.M.R and Mass Spectra indicated it to be a mixture of oligomers of 4-nonylphenol in which the value of n was 0, 1, 2 and 3. Smaller amounts of oligomers in which the value of n was 4 and 5 were also detected.

By elemental analysis the product was found to contain C, 80.4% by wt; and H, 10.6% by wt. A poly(4-nonyl phenol) species ($C_{15}H_{22}O$ $0.33H_2O$) requires; C, 80.4% by wt; and H, 10.1% by wt.

b. Preparation of poly(4-nonylphenol)di-aldehyde

A sample of poly(4-nonylphenol) (30 parts by weight), prepared as described in part (a) hereof, was stirred with hexamethylenetetraamine (20 parts by weight) in glacial acetic acid (125 parts by volume), and the temperature of the reaction mixture raised to the boiling temperature of the mixture (120°±5° C). Stirring at the boiling temperature, under reflux conditions, was continued for ten hours, the temperature was then reduced to between 80° and 85° C. and a mixture of water (50 parts by weight) and concentrated (98%) sulphuric acid (18 parts by weight) was added all at once. After stirring the mixture for three hours at 80°±2° C., the mixture was cooled to between 20° and 25° C. and poured into a stirred mixture of ice and water (1000 parts by weight). Ethylacetate (1000 parts by volume) was then added, and the mixture transferred to a separating funnel. The lower aqueous layer was removed and discarded. The upper organic layer was washed with three successive portions of water (each of 1000 parts by weight), then dried over anhydrous magnesium sulphate (100 parts by weight). The ethylacetate was evaporated under reduced pressure (20-25 Torr) to yield a red-brown viscous oil (28.9 parts by weight) which was poly (4-nonylphenol)di-aldehyde.

EXAMPLE 2

The oil obtained in part (b) of Example 1 was dissolved in industrial methylated spirits (280 parts by weight) and the solution was stirred at 25° C. Hydroxyammonium chloride (21 parts by weight) was added, followed by anhydrous potassium acetate (30 parts). The mixture was heated to boiling temperature, stirred under conditions of reflux for two hours, then cooled to 25° C. before removing the industrial methylated spirits by distillation under reduced pressure (20-25 Torr). The crude product thus obtained was dissolved in ethylacetate (200 parts by weight) and the solution washed with water (200 parts by weight). After drying the separated organic phase over anhydrous magnesium sulphate, the ethylacetate was removed by distillation under reduced pressure (20-25 Torr) to yield 17.4 parts by weight of a fawn crystalline solid, having a melting point in the range 110°-115° C.

By analysis the product was found to contain; C, 76.0% by wt; H, 9.7% by wt; and N, 3.2% by wt. An oligomeric 4-nonylphenol containing 2 terminal oximinomethyl groups, and a value of n=1.56, ($C_{55.4}H_{82.3}N_2O_{5.56}$) requires; C, 76.9% by wt; H, 9.5% by wt; and N, 3.2% by wt.

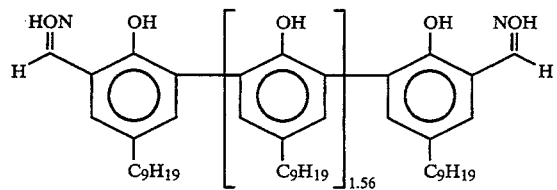

EXAMPLE 3

A sample of the product of step (a) of Example 1 (0.4534 parts by weight) was dissolved in a mixture of propan-2-ol (88 parts by weight) and water (15 parts by weight).

Samples of zinc-coated steel, obtained from British steel and labelled MINIMUM SPANGLE GALVATITE were cut into coupons measuring 4 inches by 1 inch (10.16 cm×2.54cm). These coupons were cleaned by successive immersion in a) boiling 1,1,1-trichloroethane for five minutes; b) the vapour above boiling 1,1,1-trichloroethane for 20 seconds; c) an aqueous solution of 15 gdm$^{-3}$ of RIDOLENE 1089 (a proprietary alkaline detergent for cleaning metal surfaces) for ten seconds at 60° C.; d) cold running tap water; e) cold distilled water. The coupons were then dried in a current of warm air for 30 seconds.

Three coupons cleaned in the manner described were immersed in the solution of the product of Example 1(a) for five minutes at 25° C., removed, allowed to drain for 30 seconds, then dried in a current of warm air. The edges of each coupon were coated with a protective film of butyl rubber which was allowed to dry.

Each coupon was then immersed in distilled water contained in a separate glass jar, and allowed to stand at a temperature of between 20° and 25° C.

Negative control coupons were prepared by immersing cleaned coupons in a mixture of propan-2-ol and water 950 parts by weight of each component) for 5 minutes at 25° C., then proceeding exactly as described above for the coupons treated with the solution containing the product of Example 1(a).

The distilled water in each glass jar was replaced with fresh liquid at approximate 48 hour intervals, and the extent of corrosion of each test coupon was recorded as an estimate of the area of metal which had corroded to produce encrustations of white or grey corrosion products.

The surface of the coupons treated with the solution containing the product of Example 1(a) were completed covered in corrosion products after 60 hours' immersion in the distilled water. The control coupons were completely encrusted in grey corrosion products within 24 hours.

EXAMPLE 4

A solution of the product of Example 1(a) produced as described in Example 3, was metered onto the zinc surface (coupons cleaned as in Example 3) by the use of a drawing bar (K-bar), designed to produce a wet film thickness of 24 microns, and hence an approximate dry coating weight of 50 mg m$^{-2}$ of the product. These coupons were dried in warm air and subjected to corrosion tests in exactly the same manner as described in Example 3. After immersion in distilled water for 80 hours, extensive corrosion was evident on the surface of the coupons treated with the solution of the product of Example 1(a). Negative control coupons, coated only with a mixture of propan-2-ol and water had suffered severe corrosion within 24 hours of being immersed in distilled water.

EXAMPLE 5

The product of Example 2 (0.28 parts by weight) was dissolved in propan-2-ol (92 parts by weight) and water (20 parts by weight), and applied to the surfaces of zinc-steel coupons which had been cleaned as described in Example 3. In subsequent corrosion tests, carried out as described in Example 3, complete corrosion of the surface of the coupons treated with the solution of the product of Example 2 was noted on one coupone after 186 hours, with considerably longer times to complete surface corrosion being noted for the other two coupons. Negative control coupons were completely encrusted in grey corrosion products after 24 hours.

EXAMPLE 6

Preparation of poly(4-nonylphenol)di-methylethanol aminomethyl derivative

A sample of poly(4-nonylphenol) (30 parts by weight) prepared as described in Example 1(a) hereof was dissolved, with stirring, in industrial methylated spirits (80 parts by weight). N-methylethanolamine (11.25 parts by weight) and water (10 parts by weight) were then added. This mixture was heated with stirring to 50°±2° C., and aqueous formaldehyde solution (37%w/w, 11.3 parts by weight) was then introduced over a period of 20 minutes. Stirring was continued at 50°±2° C. for three hours. The industrial methylated spirits was removed under reduced pressure (20–25 Torr), and the residues were dissolved in ethylacetate (200 parts by weight). The organic solution obtained was washed well with three successive portions (100 parts by weight) of water, dried over anhydrous magnesium sulphate, then the ethylacetate was removed by distillation under reduced pressure (20–25 Torr). The product (27 parts by weight) was found by analysis to contain: C, 77.2% by wt; H, 10.5% by wt; and N, 2.0% by wt.

EXAMPLE 7

A sample of the product of Example 6 (0.4335 parts by weight) was dissolved in propan-2-ol (153 parts by weight) and water (20 parts by weight). Samples of zinc-coated steel, obtained from British Steel and labelled MINIMUM SPANGLE GALVATITE were cut into coupons measuring 4 inches by 1 inch (10.16 cm×2.54 cm). These coupons were cleaned by successive immersion in a) boiling 1,1,1-trichloroethane for five minutes; b) the vapour above boiling 1,1,1-trichloroethane for 20 seconds; c) an aqueous solution of 15 gdm$^{-3}$ of RIDOLENE 1089 (a proprietary alkaline detergent for cleaning metal surfaces) for ten seconds at 60° C.; d) cold running tap water; e) cold distilled water. The coupons were then dried in a current of warm air for 30 seconds.

Three coupons cleaned in the manner described were immersed in the solution of the product of Example 6 for five minutes at 25° C., removed, allowed to drain for 30 seconds, then dried in a current of warm air. The edges of each coupon were coated with a protective film of butyl rubber which was allowed to dry.

Each coupon was then immersed in distilled water contained in a separate glass jar, and allowed to stand at a temperature of between 20° and 25° C.

Negative control coupons were prepared by immersing cleaned coupons in a mixture of propan-2-ol and water (50 parts by weight of each component) for 5 minutes at 25° C., then proceeding exactly as described above for the coupons treated with the solution containing the product of Example 1(b).

By way of a further comparison, a sample of the product of part (a) of Example 1 (0.4534 parts by weight) was dissolved in propan-2-ol (88 parts by weight) and water (15 parts by weight) and further control coupons were prepared by immersing cleaned coupons in this solution in the manner described for the solution of the product of Example 1(b).

The distilled water in each glass jar was replaced with fresh liquid at approximately 48 hour intervals, and the extent of corrosion of each test coupon was recorded as an estimate of the area of metal which had corroded to produce encrustations of white or grey corrosion products. The coupons treated with the solution containing the product of Example 1(b) had developed 100% surface corrosion after 150 hours' immersion in the distilled water. The negative control coupons, however, were completely encrusted in grey corrosion products within 24 hours and the further comparative coupons coated with a solution containing the product of Example 1(a) were completely encrusted in grey corrosion products within 60 hours.

EXAMPLE 8

A sample of the product of Example 6 (0.329 parts by weight) was dissolved in propan-2-ol (10 parts by weight) and added all at once to stirred water (50 parts by weight). The pH of the resultant suspension was adjusted to 4.5 by addition of a dilute aqueous phosphoric acid solution (1% w/w). Propan-2-ol was then added in a sufficient amount to produce 13 parts by weight of a clear solution.

This solution was applied to zinc steel coupons by the method described in Example 7. Coupons treated with this solution of the product of Example 6 were completely covered in surface corrosion after 277 hours' immersion in distilled water. In contrast control coupons treated only with a mixture of propan-2-ol and water showed complete encrustation with corrosion products after immersion in distilled water for 24 hours.

We claim:

1. A compound of the general formula (I)

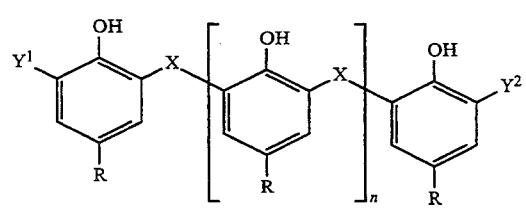

wherein

R is a substituted or unsubstituted hydrocarbon group containing from 6 to 30 carbon atoms;

$Y^1$ is a group

or a group

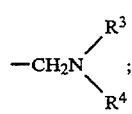

$Y^2$ is a group

when $Y^1$ is a group

or a group

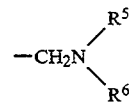

when $Y^1$ is a group

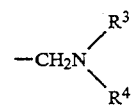

$R^1$ and $R^2$ are each independently hydrogen or a substituted or unsubstituted hydrocarbon group containing up to 20 carbon atoms;

$R^3$ and $R^5$ which may be the same or different are amino $C_{1-4}$-alkyl, mercapto $C_{1-4}$-alkyl or hydroxy $C_{1-4}$-alkyl;

$R^4$ and $R^6$ which may be the same or different are hydrogen, hydrocarbon having up to 20 carbon atoms or as defined for $R^3$ and $R^5$;

X is a direct bond; and n has a value of zero or does not exceed 10.

2. The compound of claim 1 having the general formula (II)

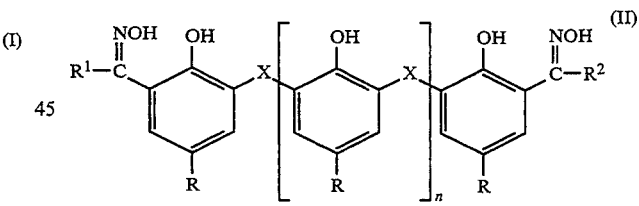

wherein R, $R^1$, $R^2$, X and n are as defined.

3. The compound of claim 2 wherein $R^1$ and $R^2$ are both hydrogen.

4. The compound of claim 1 having the general formula IV

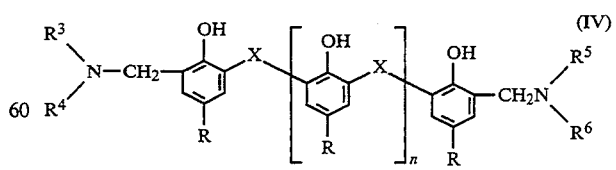

wherein R, $R^3$, $R^4$, $R^5$, $R^6$, X and n are as defined.

5. The compound of claim 4 wherein $R^3$ and $R^5$ are $C_{1-4}$ alkyl.

6. The compound of claim 4 wherein $R^4$ and $R^6$ are hydroxy $C_{1-4}$ alkyl.

7. The compound of claim 1 wherein n is between 1 and 3.

8. The compound of claim 1 wherein R is a hydrocarbon group having at least 6 carbon atoms and not more than 24 carbon atoms.

9. A compound according to claim 2 wherein R is alkyl, X is a direct bond, and $R^1$ and $R^2$ are both hydrogen.

10. A composition which comprises
 a) a liquid solvent or dispersant or a surface coating composition; and
 b) a compound as claimed in claim 1.

11. A composition according to claim 10 in which component (a) is a lubricating material and the composition is in contact with metal surfaces which are in relative motion.

* * * * *